United States Patent
Schaffer

(10) Patent No.: US 8,954,339 B2
(45) Date of Patent: Feb. 10, 2015

(54) DETECTION OF ERRORS IN THE INFERENCE ENGINE OF A CLINICAL DECISION SUPPORT SYSTEM

(75) Inventor: James David Schaffer, Wappingers Falls, NY (US)

(73) Assignee: Koninklijke Philips N.V., Eindhoven (NL)

( * ) Notice: Subject to any disclaimer, the term of this patent is extended or adjusted under 35 U.S.C. 154(b) by 609 days.

(21) Appl. No.: 12/747,595

(22) PCT Filed: Dec. 10, 2008

(86) PCT No.: PCT/IB2008/055200
§ 371 (c)(1),
(2), (4) Date: Jun. 11, 2010

(87) PCT Pub. No.: WO2009/081306
PCT Pub. Date: Jul. 2, 2009

(65) Prior Publication Data
US 2010/0280847 A1 Nov. 4, 2010

Related U.S. Application Data

(60) Provisional application No. 61/015,930, filed on Dec. 21, 2007.

(51) Int. Cl.
G06Q 50/00 (2012.01)
G06F 7/00 (2006.01)
G06F 17/30 (2006.01)
G06F 19/00 (2011.01)
G06Q 50/24 (2012.01)

(52) U.S. Cl.
CPC ............. *G06F 19/345* (2013.01); *G06Q 50/24* (2013.01)
USPC .................................. 705/3; 705/2

(58) Field of Classification Search
USPC ............................................. 705/3
See application file for complete search history.

(56) References Cited

U.S. PATENT DOCUMENTS

| 7,542,947 B2 * | 6/2009 | Guyon et al. ................... 706/12 |
| 2008/0243542 A1 * | 10/2008 | Hammond et al. ............... 705/2 |
| 2008/0281639 A1 * | 11/2008 | Quinn et al. ..................... 705/3 |

FOREIGN PATENT DOCUMENTS

| JP | 11312199 A | 4/1998 |
| JP | 2001282538 A | 3/2000 |
| JP | 2003331062 A | 5/2002 |
| JP | 2004130090 A | 7/2002 |
| JP | 05290020 B2 | 3/2009 |
| WO | 03040965 A2 | 5/2003 |

\* cited by examiner

*Primary Examiner* — Hiep V Nguyen

(57) ABSTRACT

An electronic clinical decision support system (CDSS) (10, 12) comprises: an inference engine (20, 22) configured to generate clinical decision recommendations for a patient based on information pertaining to the patient, the inference engine comprising rules (16) developed by a plurality of medical experts (14) and codified into software; an electronic outliers detector (52) configured to detect outlier cases that are probative of a potential flaw in the inference engine; an outliers database (60) configured to collect information pertaining to the outlier cases detected by the electronic outliers detector; and an outliers report generator (62) configured to generate a report (64) on the outlier cases detected by the electronic outliers detector, the generated report containing at least some information collected in the outliers database.

18 Claims, 2 Drawing Sheets

Figure 1:
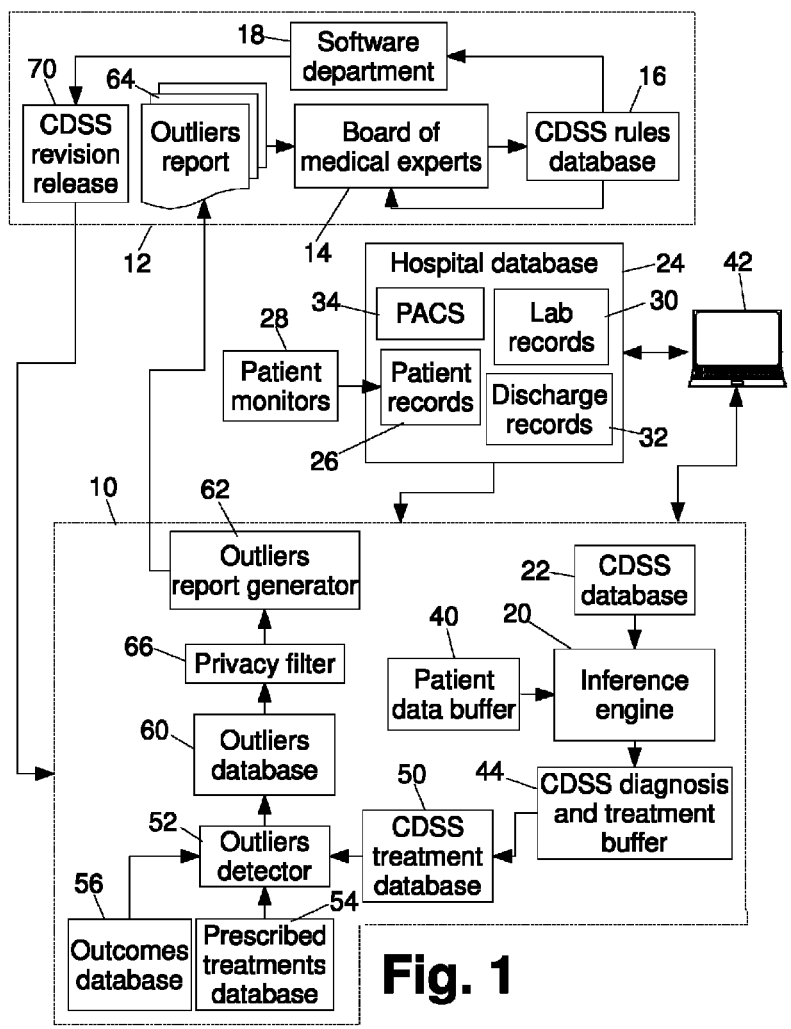

DETECTION OF ERRORS IN THE INFERENCE ENGINE OF A CLINICAL DECISION SUPPORT SYSTEM

The following relates to the medical arts, diagnostic arts, software arts, and the like.

Physicians are required to make clinical decisions on a daily basis. These decisions entail collecting information about the patient, deciding upon a diagnosis, and deciding upon a treatment for the patient. Physicians undergo years of training in order to become adept at making such clinical decisions, and rely heavily upon prior experience, education, and collected knowledge. When a physician is uncertain as to a clinical decision, he or she may consult professional colleagues, medical treatises, published medical studies, and so forth. Nonetheless, even with all these resources the complexity of some clinical decisions, and the hectic nature of hospitals and some other medical environments, can make clinical decisions difficult. This is a problem, since an erroneous clinical decision can lead to an adverse consequence for the patient, such as prolonged discomfort, temporary or permanent disability, or even death.

Electronic clinical decision support systems (CDSS) have been developed to provide support for clinical decision making. More advanced electronic CDSS systems receive patient medical information such as measured physiological parameters, patient test results, and so forth, and include an inference engine that applies predetermined diagnostic and treatment rules to the measured physiological parameters, patient test results, and so forth, to determine a diagnosis or diagnoses and to recommend one or more courses of treatment. The predetermined rules are formulated by a board of medical experts, and are encoded by computer programmers to construct the inference engine. In this way, the inference engine embodies the cumulative medical expertise of a wide range of expert physicians on a range of medical topics, and can provide diagnosis and/or a course of treatment that may not have been known to, or recognized by, the treating physicians.

A CDSS is expected to provide sound treatment recommendations in many cases. However, it is recognized that the treating physicians have additional information not available to the CDSS, and have the further advantage of directly examining the patient being treated. Accordingly, for the foreseeable future the role of CDSS systems will be advisory—the treating physicians will continue to use their own judgment, and may elect to accept, modify, or wholly disregard the CDSS recommendations.

Electronic CDSS systems with inference capability are complex systems. Because of the interrelated nature of clinical diagnosis and treatment, the rules implemented by the inference engine sometimes embody complex interactions among different rules, and a rule may be multi-pronged or have other complex structure. Such interrelatedness and complexity makes it difficult or impossible to single out and identify a flaw in a specific rule or rule portion. In view of these and other complexities, the CDSS is generally not readily amenable to ongoing incremental updating.

Rather, existing CDSS systems are generally upgraded on a periodic basis, e.g. every year or every six months, by the development and deployment of version upgrades that incorporate newly developed medical knowledge and standards. At each upgrade, a board of medical experts review the existing rules implemented by the CDSS to identify rules that should be discarded, replaced, revised, or added. The board of medical experts relies upon its cumulative expertise augmented by published medical studies or the like to make its decisions as to rule changes. Once a revised set of rules is settled upon by the board of medical experts, software programmers take over to construct the inference engine as a software program embodying the revised rules. This results in a CDSS revision release that is used to upgrade the CDSS to the new version.

This approach to updating the CDSS has certain disadvantages. First, it relies upon the expertise of the medical professionals that make up the board of medical experts. While these individuals are selected to have expansive knowledge in their respective areas of expertise, such knowledge cannot be completely comprehensive, and accordingly there remains some possibility that erroneous rules may be formulated. The interrelatedness of some rules enhances this possibility, since for example a medical expert with expertise in one area may not have knowledge of a potential adverse consequence of a treatment plan in a different area.

Moreover, even if a rule or collection of related rules is medically sound, it is possible that an error may be introduced during the software development process. If the rule is correct and the error is introduced by computer programmers codifying the rule, this error will go into the next version of the CDSS. Even worse, because the board of medical experts review the rules, rather than the generated software code, it follows that any correct but erroneously coded rule will not be detected by subsequent board reviews, and will instead remain in the CDSS unless and until a software debugging process detects the erroneous coding. But, depending upon the nature of the coding error, it may be difficult or impossible for software debugging processes to detect the erroneously coded rule. The computer programmers are generally not medical professionals and may have difficulty recognizing erroneous medically related results produced by the erroneous coding.

The following provides improvements, which overcome the above-referenced problems and others.

In at least one exemplary some embodiment, an electronic clinical decision support system (CDSS) is disclosed, comprising: an inference engine configured to generate clinical decision recommendations for a patient based on information pertaining to the patient, the inference engine comprising rules developed by a plurality of medical experts and codified into software; an electronic outliers detector configured to detect outlier cases that are probative of a potential flaw in the inference engine; an outliers database configured to collect information pertaining to the outlier cases detected by the electronic outliers detector; and an outliers report generator configured to generate a report on the outlier cases detected by the electronic outliers detector, the generated report containing at least some information collected in the outliers database.

In at least one embodiment disclosed herein as an illustrative example, a method is disclosed for operating an electronic clinical decision support system (CDSS) including an inference engine comprising software configured to generate clinical decision recommendations in accordance with clinical decision rules, the method comprising: generating clinical decision recommendations for patient cases using the inference engine; detecting outlier cases comprising a subset of the patient cases for which the inference engine generated clinical decision recommendations likely to be probative of one or more potential flaws in the inference engine; and collecting information pertaining to the outlier cases.

In at least one embodiment disclosed herein as an illustrative example, a computer readable medium is disclosed that carries computer code configured to control a processor to perform the method of the preceding paragraph.

In at least one embodiment disclosed herein as illustrative example, a monitoring system is disclosed for monitoring an electronic clinical decision support system (CDSS) including an inference engine comprising software configured to generate clinical decision recommendations in accordance with clinical decision rules, the monitoring system comprising: an electronic outlier detector configured to detect outlier cases comprising a subset of patient cases for which at least one of the following holds: (i) the inference engine generates a clinical decision recommendation that is not followed and (ii) the inference engine generates a clinical decision recommendation and the patient outcome is poor; and an outlier database configured to collect information pertaining to the outlier cases detected by the electronic outliers detector.

One advantage resides in more efficient CDSS upgrading.

Another advantage resides in detection of software coding errors in an operational CDSS system.

Another advantage resides in more effective CDSS upgrading by providing of a compact set of high value data to medical experts revising the CDSS.

Still further advantages will be appreciated to those of ordinary skill in the art upon reading and understand the following detailed description.

The drawings are only for purposes of illustrating the preferred embodiments, and are not to be construed as limiting.

FIG. 1 diagrammatically shows an electronic clinical decision support system (CDSS) including an inference engine and upgrade components.

Figure 2:
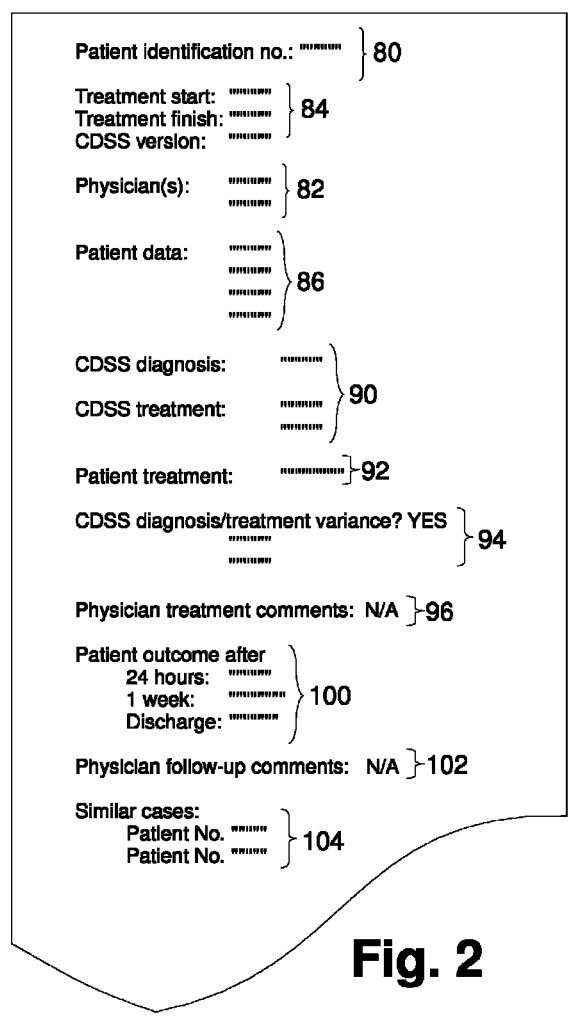

FIG. 2 diagrammatically shows a page of an illustrative format of an outliers report generated by the outliers report generator of the electronic CDSS of FIG. 1.

With reference to FIG. 1, an electronic clinical decision support system 10, 12 includes a main operational portion 10 and an upgrade portion 12. The operational portion 10 is operative on a continuous daily basis to provide support for clinical decisions. The upgrade portion 12 is applied occasionally, such as every six months, every year, every two years, and so forth, so as to keep the operational portion 10 up-to-date with developments in the relevant diagnostic and treatment fields, and to correct errors detected based on analysis of outliers detected by the operational portion 10. The operational portion 10 of the electronic CDSS 10, 12 is substantially automated, but may also incorporate some manual interaction such as manual input of patient data, manual interaction with the decision support process (e.g., a manual selection from amongst a limited set of options presented by the CDSS) and so forth. Such manual interaction may also include the treating physician electing not to adopt some or all recommendations provided by the operational CDSS portion 10, and optionally providing a written or otherwise articulated explanation of the reasons for not adopting them. The upgrade portion 12 of the electronic CDSS 10, 12 is semi-automated, but includes substantial manual input and processing provided by a board of medical experts 14 (where this term is intended to be broadly construed to encompass any group, collection, or other plurality of medical experts, the experts typically being licensed physicians but optionally also including licensed nurses, unlicensed medical practitioners, engineers or scientists working in medically related fields, experts drawn from academia, radiological experts, and so forth) who generate and occasionally evaluate or review a CDSS rules database 16 comprising a plurality of rules. Additionally, the upgrade portion 12 includes substantial manual input from a software department 18 (where this term is intended to be broadly construed to encompass any collection of one or more computer programmers, computer scientists, computer analysts, database experts, or the like, any organization including such persons, any company, corporation, or other entity including such persons) that codifies the CDSS rules database 16 into software.

It should also be noted that either or both of the board of medical experts 14 and/or the software department 18 may have a composition or identity that changes with time, as for example some medical experts join the board 14 while other medical experts resign from or otherwise leave the board 14. As another example, the software department 18 may change identity if, for example, the organization employing the electronic CDSS 10, 12 terminates a software development contract with one software company and instead hires a different software company to perform the next upgrade, or performs the next upgrade using in-house software expertise. Still further, while both the board of medical experts 14 and the software department 18 include human actors providing processing, it is also contemplated for either or both of the board 14 and/or the software department 18 to include automated or semi-automated components, such as electronic medical databases, electronic search engines configured to search medical journals, compilers that convert high-level software programming into a lower-level code, and so forth. Another contemplated automated or semi-automated component is inclusion of a machine learning technology to automatically adjust rules so that CDSS system behavior is improved.

A principal component of the operational portion 10 is an inference engine 20, which is configured to generate clinical decision recommendations for a patient based on information pertaining to the patient. The inference engine 20 is generated by the software department 18, and incorporates the rules of the CDSS rules database 16 (formulated by the board of medical experts 14) in codified or software form. The inference engine 20 also includes software providing user interfacing and processing to enable input of patient data and applying of the codified rules to the patient data in order to compute or infer medically relevant inferences from the patient data. The term "software" is intended to be broadly construed to encompass any collection or set of instructions executable on a computer, processor, controller, personal data assistance, or other digital device, and is intended to encompass such instructions stored on any digital storage medium such as a magnetic disk, an optical disk, magnetic tape, solid-state read/write memory such as FLASH memory, a read-only memory (ROM), a random access memory (RAM), and so forth, or any combination of storage media. The codification of the CDSS rules database 16 included in the inference engine 20 may entail conventional programming, or may entail any other operation that results in executable instructions, such as development of an interactive relational or other database, a rules-based logic programming language such as Prolog, or so forth. Still further, the executable instructions of the inference engine 20 may be directly executable machine code, an intermediate binary code such as Java byte codes, software instructions stored in a higher level interpretive language such as BASIC whose English-like instructions are compiled "on-the-fly" by interpreter software running on the computer or other digital device, or so forth. Still further, it is to be understood that the physical location of the inference engine 20 is not important. The inference engine 20 may be operating on a computer located at a hospital or other medical facility, or may be operating on a remote server accessed by medical personnel at the hospital or other medical facility via the Internet, and so forth. In addition to the inference engine 20, the operational portion 10 of the electronic CDSS 10, 12 optionally includes other components such as a CDSS database 22 that stores look-up tables, physical constants, anatomical models, or other data that is accessed and used by the inference engine 20 in implementing the CDSS rules database 16.

In operation, a treating physician or physicians (where the term "treating physician" is to be broadly construed as encompassing any person or plurality of persons making a clinical decision, such persons typically being licensed physicians but also contemplated to encompass licensed or unlicensed nurses, school nurses, athletic trainers, clinical radiologists, or so forth) is faced with a clinical decision regarding a patient. Some typical settings where this may occur include hospital emergency rooms, a doctor's office, a sports facility at which a player has been injured, a school nurse treating a student complaining of a discomfort, or so forth. In the embodiment illustrated in FIG. 1, an illustrative hospital setting is diagrammatically depicted, which includes a hospital database 24. Hospital database 24 stores for example medically-related and patient-related information such as patient records 26 (some of which are optionally automatically received and stored from patient monitors 28 via a wired, wireless, or combination of wired and wireless local area networking) and laboratory records 30 having information acquired by diagnostic laboratories such as blood test labs, x-ray labs, and so forth. Such stored information is optionally linked with or copied into the corresponding patient records 26, discharge records 32 respective to discharged (or, in some embodiments, deceased) patients, a picture archiving and communications service (PACS) 34 storing medical images acquired by magnetic resonance imaging (MRI), computed tomography (CT), positron emission tomography (PET), and so forth. The illustrated hospital database 24 is an example, and other hospital databases may include more, less, or different information than that illustrated, or may organize the information differently, or may include multiple separate databases, and so forth. As with the system executing the inference engine 20, the hospital database 24 may be on-site or located remotely, e.g. accessed via the Internet. Moreover, in some embodiments the same computer system or other digital device or system stores and executes both the hospital database 24 and the operational portion 10 of the CDSS 10, 12.

The treating physician or physicians faced with the clinical decision may opt to make use of the operational portion 10 of the CDSS 10, 12. Rather than opting to use the CDSS however, it is contemplated that in some embodiments the treating physician or physicians may be required to use the CDSS by hospital regulations, jurisdictional laws, or the like. To do so, the patient data is collected and stored in a patient data buffer 40 so that it can be supplied to the inference engine 20. This patient data is collected in various ways. For example, the operational portion 10 of the CDSS 10, 12 may automatically retrieve relevant patient data from the hospital database 24 via a digital network such as a hospital network or the Internet, or by direct access if the hospital database 24 and CDSS operational portion 10 are both stored and executed on the same computer or other common digital device and the CDSS process has read-access permission respective to the hospital database 24. Additionally, the treating physician or physicians, or another human operator, may input the patient data directly into the hospital database CDSS operational portion 10 using a user interface 42. (The user interface 42 may be a desktop or laptop computer, a dumb terminal, a personal data assistant, or so forth, and while a single representative user interface 42 is depicted in FIG. 1 it is to be appreciated that a typical hospital or other medical setting may include several, dozens, hundreds, or more user interfaces at various locations throughout the hospital, and further that the user interface may optionally be located outside of the hospital). Patient data may also be collected from other sources, such as read off of an optical disk, retrieved from a remote database via the Internet, copied off of an ambulance-based computer or device, read directly from the patient monitors 28 via a wired or wireless communication link, and so forth.

The information contained in the patient data buffer 40 is analyzed by the inference engine 20. If additional information is needed or would be useful in order for the inference engine 20 to make a clinical decision recommendation, the inference engine 20 may attempt to acquire such information either automatically (for example, by accessing the hospital database 24 or reading data directly from the patient monitors 28) or by making a request for such additional information via the user interface 42. The inference engine 20 is configured to provide recommendations within a selected scope of expertise defined by the scope of the rules of the CDSS rules database 16 that are incorporated in into the inference engine 20. For example, the inference engine 20 may have an operational scope encompassing only cardiac problems, or only cardiopulmonary or vascular problems. Alternatively, the inference engine 20 may have an operational scope encompassing substantially the entire field of clinical medicine. The scope of the inference engine 20 is defined by the scope of the CDSS rules database 16, which can be made as broad or as narrow as desired, based on the cumulative expertise of the board of medical experts 14. The treating physician or physicians may alternatively constrain operation of the inference engine 20 by inputting some constraints on the clinical decision to be made. For example, in some embodiments the treating physician or physicians may select the general area of the clinical decision to be made from a menu of decision options displayed on the user interface 42. As an example, the menu may provide a list including: "torso pain or discomfort"; "abdominal pain or discomfort"; "respiration problems", and so forth. Alternatively or additionally, the general area of the clinical decision to be made may be inferred from the patient data.

If insufficient data is provided, or if the area of the clinical decision to be made is outside of the scope of the inference engine 20, then the inference engine 20 suitably reports this to the treating physician or physicians via the user interface 42. On the other hand, if the inference engine 20 receives sufficient patient data and the clinical decision is within the scope of the CDSS rules database 16, then the inference engine 20 applies relevant rules of the CDSS rules database 16 (in codified software form) to the patient data to generate a clinical decision recommendation (typically comprising a recommended diagnosis or diagnoses and one or more recommended courses of treatment) that is stored in a CDSS diagnosis and treatment buffer 44 and preferably formatted and articulated on the user interface 42 in the form of readily comprehensible English or another natural language, optionally augmented by images, diagrams, models, or other graphics, simulated voice exposition, or other output that may be helpful in articulating the clinical decision recommendation.

The CDSS rules database 16 can take various forms. For example, a rule for addressing diagnosis and treatment of detected lung cancer nodules could be formulated as follows. By considering morphological and textual features of a suspicious nodule imaged by computed tomography, an estimate of the likelihood that the suspicious nodule is cancerous can be made. For example, this likelihood could be expressed as a probability lying in the range [0,1] where higher values indicate higher likelihood of malignancy. Based on this likelihood, a diagnosis is readily presented to the treating physician, possibly along with a confidence measure computed based on the likelihood. A treatment recommendation is suitably selected based on computation of expectation of success for specific medical actions that have been used in the past for such cases. Fuzzy logic is one way to compute the expectations of success. For instance, one might define family membership functions such as, "the expectation for ordering a biopsy would be HIGH if P(malignant)>0.85, MODERATE if P(malignant)>0.65, and LOW if P(malignant)<0.65." Similar expectations could be defined for other clinical options such as, order a follow-up computed tomography examination in six months, and so forth. A recommended course of treatment is selected as one, or a combination, of these medical actions.

In another approach, the CDSS rules database 16 may comprise rules for identifying similar cases from the hospital database 24. Such a rule can be constructed, for example, by assigning importance weights to different patient data, and determining similarity as a sum of the similarity of each corresponding characteristic weighted by the importance weight for that characteristic. Some patient data that may be suitably incorporated into such a weighted combination may include, for example: patient-descriptive characteristics such as age, weight, ethnicity, or sex; monitoring data such as heart rate, blood pressure, or respiratory rate; symptoms such as chest pain (and possibly a measure of its acuteness), breathing difficulty, or sleeping difficulty; and so forth. Some such weights may be binary parameters, e.g. either the patient has a suspicious lung nodule or does not. Some such binary weights could be used as filters rather than weights—e.g., in considering a patient having a suspicious lung nodule, it makes sense to omit from consideration as a "similar case" any other patient for whom no suspicious lung nodule has been identified. By using such a rule to identify similar cases, the treatment recommendation can be given as the treatment used in the most similar case that had a successful outcome, or as some combination of the treatments in the N most similar cases having successful outcomes.

The clinical decision recommendation is reported to the treating physician or physicians via the user interface 42, and is also stored in a CDSS treatment database 50 which tracks the clinical decision recommendations made by the operational portion 10 of the CDSS. The operational portion 10 further includes outlier detector 52, whose purpose is to identify "outlier" cases, which are a subset of the patient cases processed by the operational CDSS portion 10 that are detected as having a substantial possibility of being probative of possible flaws in the inference engine 20.

The term "a flaw in the inference engine" is to be broadly construed as encompassing any error in the CDSS rules database 16, any error in the codification of these rules into software, as well as any error in look-up tables or other reference information contained in the CDSS database 22 and by the inference engine 20 in generating the clinical decision recommendation. The term "a flaw in the inference engine" does not encompass errors in the patient data provided to the inference engine 20 via the patient data buffer 40 (although it is to be appreciated that some rules of the CDSS may be formulated to ensure reasonableness of inputted patient data, e.g. a rule may flag any input patient heart rate above 250 beats-per-minute as likely to be an erroneous input, and in such cases a "flaw" may comprise a less-than-ideal rule that questions reasonable patient data or fails to question clearly unreasonable patient data), and also does not encompass any physician error in executing the clinical decision recommendation rendered by the CDSS operational portion 10 (although it is again to be appreciated that some rules of the CDSS may be formulated to recognize and warn of commonplace treatment implementation errors based on patient input data received subsequent to initiation of patient treatment, and a "flaw" in such cases may comprise a less-than-ideal rule that raises frivolous questions about the treatment implementation or fails to recognize clearly improper treatment implementation).

Furthermore, a decision by the physician to override or ignore the clinical decision recommendation rendered by the CDSS operational portion 10 is not to be construed as a flaw in the inference engine, except if such a decision to override or ignore was motivated or influenced by a deficiency in the articulation of the recommendation by the CDSS operational portion 10, the articulation of the recommendation being considered to be a part of the codified inference rules. A deficiency in articulation qualifying as a flaw in the inference engine may be an erroneous articulation (e.g., the articulation of the recommendation does not accurately represent the recommendation) or may be a correct but unconvincing articulation (e.g., the articulation of the recommendation is factually correct, but is so poorly presented that the physician does not appreciate the soundness of the recommendation). For example, a recommendation stating merely "Apply body cooling to induce moderate hypothermia" might be deemed to be a flaw in the inference engine because a reasonable treating physician might elect not to follow this terse and potentially harmful recommendation. On the other hand, a recommendation correcting this flaw might read: "The symptoms suggest a spinal injury that is likely to induce dangerous swelling with a high likelihood of leading to permanent partial paralysis or death. It is recommended to apply body cooling to induce moderate hypothermia so as to reduce the swelling. See . . . " where the " . . . " provides a citation to a relevant medical study.

The outliers detector 52 monitors the CDSS treatment database 50 so as to detect outlier cases that may be probative of a flaw in the inference engine 20, which in this context include the CDSS database 22. Outlier cases can be detected using substantially any outlier detection criterion or criteria that identify potentially probative cases. Because medicine is an inexact science, detection of an outlier case is not trivial. There may be patient cases for which the CDSS provided a sound treatment recommendation, and yet there was an adverse outcome. Conversely, there may be patient cases for which the CDSS provided an unsound treatment recommendation, and yet the patient had a good outcome. Moreover, the determination of the outcome can be ambiguous—for example, if a patient comes into the hospital in critical condition, and remains in critical condition for several weeks, but eventually recovers, the determination of whether this was a "good" outcome or a "poor" outcome is dependent upon a wide range of factors and considerations.

As one example, the outliers detector 52 uses the following set of rules to detect outlier cases. An outlier case is one which satisfies one of the following three conditions:

A. The CDSS provided a recommendation which was not followed, and yet the outcome was good.
  B. The CDSS provided a recommendation which was not followed, and the outcome was poor.
  C. The CDSS provided a recommendation that was followed, but the outcome was poor.

The rationale behind this outlier criterion is as follows. In any case satisfying condition A, there is a likelihood that the treating physician identified a flaw in the CDSS treatment recommendation, which is why the physician overrode the CDSS treatment recommendation. The fact that the actual treatment was successful provides further suggestion that the treating physician may have had some valuable insight. Thus, patient cases satisfying condition A are suitably detected as outlier cases.

In any case satisfying condition B, the treating physician again presumably believed there was some flaw in the CDSS recommendation. Because the actual treatment provided a poor outcome, there is a higher likelihood that the treating physician was wrong in deciding to override the CDSS recommendation as compared with cases satisfying condition A. But, there remains a substantial possibility that the physician in a case satisfying condition B had some valuable insight or recognition into some flaw in the CDSS treatment recommendation. Moreover, even if the CDSS treatment recommendation was sound and the treating physician used poor judgment in overriding it, consideration of a patient case satisfying condition B may be useful in determining whether the inference engine 20 is flawed in its articulation of the CDSS treatment recommendation. In other words, perhaps the CDSS treatment recommendation could have been articulated more clearly so that the treating physician would have seen the soundness of the recommendation.

Any case satisfying condition C is an outlier because the poor outcome in spite of the treating physician following the CDSS treatment recommendation provides substantial evidence that there may be a flaw in the treatment recommendation.

The three conditions A, B, C can be reduced to two simpler conditions as follows:
1. The CDSS provided a recommendation which was not followed.
2. The CDSS provided a recommendation which was followed, but the outcome was poor.

Advantageously, by reformulating the outlier criterion using conditions (1), (2), the result is that condition (1) can be used to identify some outlier cases without consideration as to the patient outcome. This can be advantageous because the treating physician or his or her professional colleagues may be reluctant to categorize the outcome as poor, especially since the treating physician acted affirmatively and independently to override the CDSS treatment recommendation. Thus, it may be that in some cases only the actual treatment recommendation is available, but no useful patient outcome measure is available.

Condition (2) is outcome-dependent. However, condition (2) can hold only when the treating physician followed the CDSS treatment recommendation. As a result, the treating physician acted in accord with the CDSS treatment recommendation, and accordingly may be more willing to characterize the patient outcome as poor if appropriate.

In some cases, patient outcome may be unavailable. For example, the hospital may be unwilling to characterize any outcome as poor in view of potential malpractice liability. Additionally, as noted previously it can be difficult to assess whether an outcome is good or poor. In such cases, it is contemplated to use an outlier criterion that includes only condition (1).

In other contemplated embodiments, an outlier criterion may be used that includes only a single condition: Any patient case for which the CDSS provided a treatment recommendation and the outcome was poor is detected as an outlier case. This criterion is advantageously independent of the actual treatment, and may be useful in conjunction with CDSS system having inference engines that produce a complex recommended course of treatment, for example including two or more distinct and separate treatment actions (e.g., recommend to provide intravenous fluid and put the patient on medication "X"). In such systems, determination of whether the complex multiple-component treatment plan was followed could be ambiguous (e.g., if the treating physician placed the patient on intravenous fluid but elects not to prescribed medication "X", then the recommended treatment was only partially followed).

Another contemplated outlier criterion is a user-defined outlier criterion designed to have the outliers detector 52 identify patient cases with certain characteristics of interest. For example, the board of medical experts 14 may request an outlier criterion that collects cases that activate certain rules that may be tentative, or to collect statistics on certain rare conditions to provide data for formulating new rules to be implemented in a later revision of the CDSS rules database 16. For example, an outlier criterion may detect as an outlier case any patient having sickle cell anemia, or may detect as an outlier case any patient for which the CDSS applies a certain rule or collection of rules diagnosing based on a particular symptom.

The foregoing are illustrative examples of outlier criteria, and other outlier criteria may be applied dependent upon the information available. For the illustrative criterion employing conditions (1) and (2), the CDSS operational portion 10 suitably includes a prescribed treatments database 54 providing the actual treatment information used in evaluating condition (1) and a patient outcomes database 56 providing the outcome information used in evaluating condition (2). In some embodiments, patient outcome may be determined at more than one point in time, such as at twenty-four hours after patient admission into the hospital; at one week after patient admission; and at patient discharge (broadly construed as encompassing patient death). In such an embodiment, condition (2) may be deemed to be satisfied if the patient outcome is poor at any one or more of these multiple determination points.

Information pertaining to outlier cases detected by the outliers detector 52 are collected in an outliers database 60, for consideration by the board of medical experts 14 during the next CDSS revision process. For example, if a new CDSS revision is released on a yearly basis, then the outliers database 60 may collect information pertaining to outlier cases for nine months. As used herein, information collected in the outliers database 60 is intended to be construed as including information stored in the database 60 as well as information that may be stored elsewhere but incorporated into the outliers database 60 by a pointer or other reference. For example, the outliers database 60 may include a link or pointer to the patient record 26 rather than containing a copy of the record contents—in such a case, the linked contents of the patient record 26 are deemed to be content collected or stored in the outliers database 60. At a selected time, an outliers report generator 62 is invoked to generate an outliers report 64. In some embodiments, a privacy filter 66 is interposed between the outliers database 60 and the outliers report generator 62 (or elsewhere in the report formatting processing path) to filter out any information that might compromise patient privacy. For example, in a U.S. installation the privacy filter 66 may be an HIPAA-compliant privacy filter that removes any information that might identify a particular patient (e.g., name, address information, employment information, or so forth) so as to ensure that the outliers report 64 complies with the patient privacy provisions of the Health Insurance Portability and Accountability Act (HIPAA). In other embodiments, the outliers report 64 includes some patient-identifying information, but is kept confidential by the board of medical experts 14.

A plurality of operational CDSS portions 10 may be deployed at different hospitals or other medical settings, and the upgrade portion 12 may be a singular installation. For example, the upgrade portion 12 may be embodied at a software vendor's facility, and the operational CDSS portions 10 may be installations deployed at a plurality of hospitals or other medical settings that have purchased, leased, or otherwise acquired the operational CDSS portions 10 from the vendor. In such a case, the outliers report 64 is optionally generated using the combined accumulated content of the outliers databases 60 of the plurality of operational CDSS portions 10, each of which suitably transmits its collected outlier case data to the singular upgrade portion 12 via a secure Internet connection or another secure connection, optionally after filtering by the privacy filter 66. In this way, the outliers report 64 includes the accumulated content of the plurality of installed outliers databases 60.

The revision process is performed by the upgrade portion 12 of the CDSS 10, 12. During the CDSS revision process, the board of medical experts 14 revises the rules of the CDSS rules database 16 based on the outliers report 64 and other available information such as recent medical journal articles, new knowledge accumulated by the board members, information on newly acquired or newly accessible medical equipment, and so forth. Based on the outliers report 64, the board of medical experts 14 may identify a rule that is not medically sound, as evidenced by certain outlier cases in which the rule was correctly implemented by the inference engine 20 to produce a treatment recommendation in accordance with the rule, but the physician prescribed a different and (as determined by the board 14) better treatment than the one recommended by the rule. Based on the outliers report 64, the board of medical experts 14 may also identify a rule that is not medically sound, as evidenced by certain outlier cases in which the rule was correctly implemented by the inference engine 20 to produce a treatment recommendation in accordance with the rule, and the physician followed the recommended treatment, but the patient outcome was nonetheless poor.

Additionally, the board of medical experts 14 may identify, based on the outliers report 64, a rule that is medically sound, but which was not correctly codified by the programming department 18. Such a situation may be evidenced in the outliers report 18 by certain outlier cases in which the inference engine 20 produced a treatment recommendation that was either not followed by the physician, or was followed but produced a poor patient result. Upon reviewing the patient information provided by the outliers report 64, the board may determine that the treatment recommendation generated by the CDSS is not in accordance with the rules 16. This identifies a codification error that should be corrected by the software department 18 during the next revision.

The result of the revision process is a CDSS revision release 70 that embodies the rules changes developed by the board of medical experts 14, as well as any codification corrections that correct erroneous codification of medically sound rules. The CDSS revision release 70 is used to upgrade the software codified CDSS rules database of the inference engine 20 and the CDSS database 22 to correct unsound rules or codification errors. The CDSS revision release 70 may also include other changes, such as upgraded user interface dialogs, improved coding to enhance speed, migration to a new hardware platform, and so forth.

The CDSS revision release 70 may be optionally validated prior to deployment using some or all of the outlier cases of the outliers database 60. The outliers cases accumulating in the outliers database 60 provide a suitable database for validation of the new revision release 70. Such validation is suitably automated using a testbed implementation of the CDSS (for example, on the hospital computer, or on dedicated testbed computing facilities at a vendor's facility). The testbed operational CDSS portion is updated with the new revision release 70 and receives as input outlier cases accumulated in the outliers database 60. Results of interest generated by the testbed CDSS implementation, such as outputs that are different from the output from those of the previous revision or outputs that are different from those expected by the medical experts based on the revised rules, are flagged for manual review by the board of medical experts 14 and optionally by the software department 18. This validation process may be performed iteratively to adjust the rules and correct codification errors until the validated CDSS revision release 70 provides sound diagnostic and treatment recommendations for most or all of the outlier cases accumulated in the outliers database 60. The validated CDSS revision release 70 is then deployed for use in providing clinical decision support for new patient cases. The use of the outliers database 60 as a validation database for each new CDSS revision release 70 advantageously leverages the accumulation of outlier cases to provide incremental CDSS improvement, such that the ability of the CDSS to provide sound diagnosis for outlier cases improves progressively over time.

The outlier detection criterion is designed to be generally overinclusive. Such an overinclusive criterion may miss some cases that are probative of potential flaws in the inference engine. For example, the illustrative criterion based on conditions (1) and (2) will miss any case in which the recommended course of treatment was medically unsound and was followed, but the patient outcome was nonetheless satisfactory. However, the more common situation is that a patient case may satisfy the generally overinclusive outlier detection criterion, but not be probative of any flaw in the inference engine. For example, condition (1) will detect as an outlier case any patient case in which the treating physician overrides a sound and well-articulated CDSS treatment recommendation, even though such cases are not probative of any flaw in the inference engine.

By using generally overinclusive outlier detection rules, the CDSS revision process relies upon the expertise of the board of medical experts 14 in making the final determination as to which patient cases are actually probative of flaws in the inference engine. This is advantageous because these medical experts can take into account numerous factors that cannot be considered by an outlier detection algorithm, and can take into account information not readily reduced to a formula, such as interviews with the treating physicians. Moreover, the board of medical experts 14 may be able to acquire more information in the case of a poor outcome than is obtained by self-reporting alone without encouragement. The purpose of the outliers report 64 is to efficiently bring a compact set of high value data to the board 14 for its consideration when reviewing and revising the current version of the CDSS. Moreover, the provided outliers are useful in detecting codification errors, since the board of medical experts 14 is well qualified to recognize when the recommendation provided by the CDSS in at variance from the rules constructed by the board 14.

With reference to FIG. 2, a suitable illustrative format for the outliers report 64 is presented as an example. The report includes a patient identification number 80, which is a tracking number that enables the patient to be tracked while maintaining the patient's privacy. Alternatively, if the board of medical experts 14 is of sufficiently limited access, the actual patient name or other patient identification information may be provided. The illustrative outliers report format also provides the name or names of the treating physician or physicians 82, and/or other suitable medical personnel contact information.

By providing patient identification 80 and identification of medical contact personnel 82, the board of medical experts 14 can elect to follow up on the case if it appears relevant to the CDSS revision process. For example, the board 14 may elect to interview the treating physicians to obtain the physician's insights into the outlier case, and/or may elect to contact the patient to obtain further information from the patient, or to ask for permission to review the patient's records for possibly relevant information.

The illustrative format for the outliers report 64 further provides date information 84 about the outlier case, including in the illustrated example the treatment start and finish dates (e.g., date of hospital admission and discharge, for an in-patient) and the CDSS version. The latter information may be used to filter older outlier cases stored in the outliers database 60 from the outliers report 64. Alternatively, outlier cases in the last two or three revisions may be included in the outliers report 64 to provide more data to the board 14. Outlier cases from previous revisions may be retained in the outliers database 60 for use when testing the new revision release 70 using a testbed CDSS implementation. Retention of at least some outlier cases across revisions provides a quality control check on the newer revisions, as well as a larger database for the testbed. Including the CDSS version information in the outliers report 64 also enables the board 14 to recognize "carry-over" cases that are carried over from a previous version update to provide longer term monitoring of certain classes of outliers that may be under a watch.

Insofar as possible in view of privacy concerns and legal considerations, the outliers report 64 preferably provides a summary of patient data 86, which may include classification data (e.g., gender, age, ethnicity, and so forth), physiological monitoring data (e.g., pulse rate readings, $SpO_2$ readings, and so forth), laboratory test results for the patient, and other substantially objective information about the patient. Although in diagrammatic FIG. 2 the patient data 86 is indicated by a few representative lines, it is contemplated for the patient data section 86 for each outlier case to occupy multiple pages of the report, since this information can be voluminous and is of substantial value to the board of medical experts 14 in making a determination as to the probative nature, if any, of the outlier case regarding potential flaws in CDSS inference engine. Moreover, it is to be understood that the outliers report 64 may be reviewed in either printed or electronic form; in the latter case, it is contemplated for the outliers report 64 to be displayed on a computer monitor or other electronic display device without printing, and may be retrieved for electronic display from a suitable electronic storage such as the hospital database 24, or a local storage medium such as the hard disk of a reviewing medical expert's personal computer. Display or printing of the outliers report 64 may optionally also entail accessing and utilizing library programs, "helper" programs, or the like—for example, image display software of the PACS 34 may be utilized to display images related to an outlier case.

The outliers report 64 also provides the clinical decision recommendation 90 generated by the inference engine 20 for a patient. In the illustrated example, the clinical decision recommendation 90 includes a CDSS diagnosis and a CDSS treatment recommendation. The actually prescribed course of treatment 92 is also provided. Optionally, a CDSS diagnosis/treatment variance summarization 94 is also provided, which if given identifies the differences (if any) between the prescribed treatment and the CDSS recommendations. This optional variance summary is contemplated to be useful to the board of medical experts 14, who may have dozens or even hundreds, or more, outlier cases to review. In such a high workload environment, the variance summarization 94 can be useful to enable the board 14 to quickly ascertain whether the outlier case under current review is one in which the CDSS recommendation was followed, or one in which the treating physicians elected to override the CDSS recommendation. As a further aid, the outliers report 64 optionally includes a physician treatment comments section 96 (in the example illustrated in FIG. 2, the physician provided no comments, hence the "N/A" notation for this entry of the report). The treating physician's comments, if available, can be valuable to the board 14 in understanding the insights of medical personnel who actually examined the patient. On the other hand, as noted previously, in some cases the treating physician may be reluctant to provide comments in writing, and so the physician treatment comments section 96 may have an "N/A" notation or the like as illustrated. If appropriate, the board 14 may elect to contact the treating physician directly (given the physician's name and optional contact information in the section 82), and an oral interview conducted (either voluntarily or, in some embodiments, mandatory for example under the physician's hospital privileges agreement) to obtain the treating physicians' insights.

The outliers report 64 also provides patient outcome information 100, if available. This information can be of various forms and can contain various content, depending upon what information (if any) is available about patient outcome. In some embodiments, patient outcome information is obtained electronically from the salient entry or entries in the patient discharge electronic record. In some embodiments, patient outcome information is obtained electronically from other portions of the patient record 26. In some embodiments, patient outcome information is obtained manually, for example from a self-reporting form filled out by the treating physician. In some embodiments, some combination of these or other patient outcome information may be obtained and reported. In the illustrated embodiment, multiple patient outcomes 100 are reported, corresponding to different times, e.g. 24 hours after patient admittance into the hospital, one week after patient admittance into the hospital, and at discharge. In some cases, only one or some of these different patient outcomes are relevant and/or available. This can be useful since the patient outcome may be different at different times (e.g., there may be no improvement, or degradation, in patient condition in the first 24 hours, but substantial improvement over the first week.) An entry may also be provided for follow-up comments by the treating physician 102 regarding the patient outcome, if available (in the illustrated example of FIG. 2, no comments were available, hence the "N/A" notation). As with treating physician comments on the prescribed diagnosis, physician comments on the patient outcome 102 are valuable to the board 14, but may be difficult to obtain in some instances.

The outliers report 64 optionally may include different, additional, or other information selected for its potential value to the board of medical experts 14 in evaluating the significance of the outlier case respective to potential flaws in the inference engine 20 including the CDSS database 22. In the illustrated example, other information provided includes a crosslinks section 104 providing cross-indexing with other similar cases. In some embodiments, the "similar cases" may be limited to similar outlier cases, whereas in other embodiments the "similar cases" may include other patient cases for which the CDSS provided recommendations but which did not qualify as outlier cases. The cross-links section 104 can be useful in identifying other cases that may be relevant to determining potential flaws in the inference engine.

The preferred embodiments have been described. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An electronic clinical decision support system (CDSS) comprising:
    an inference engine configured to generate clinical decision recommendations for a patient based on information pertaining to the patient, the inference engine comprising rules developed h a plurality of medical experts and codified nun software, the inference engine includes a software error comprising a sound rule incorrectly codified into software;
    an electronic outliers detector configured to detect outlier cases that are probative of a potential flaw in the inference engine;
    an outliers database configured to collect information pertaining to the outlier cases detected by the electronic outliers detector;
    an outliers report generator configured to generate a report on the outlier cases detected by the electronic outliers detector, the generated report containing at least some information collected in the outliers database; and
    a revision release configured to update the inference engine, the revision release comprising update software generated by (i) identifying the software based on review of the report on outlier cases, and (ii) configuring the update software to remove the software error from the inference engine;
    wherein the inference engine, the electronic outliers detector, and the outliers report generator comprise a digital device executing software.

2. The electronic CDSS as set forth in claim 1, wherein the electronic outliers detector is configured to detect an outlier case as any case for which at least one of the following criteria hold: (i) a clinical decision recommendation was generated by the inference engine and was not followed; or (ii) a clinical decision recommendation was generated by the inference engine and the patient had a poor outcome.

3. The electronic CDSS as set forth in claim 1, wherein the electronic outliers detector receives as input a patient outcome recorded during patient discharge, and any case having a poor patient outcome recorded during patient discharge is detected as an outlier case.

4. An electronic clinical decision support system (CDSS) comprising:
    an inference engine configured to generate clinical decision recommendations for a patient based on information pertaining to the patient, the inference engine comprising rules developed by a plurality of medical experts and codified into software;
    an electronic outliers detector configured to detect outlier cases that are probative of a potential flaw in the inference engine, wherein:
        the electronic outliers detector receives as input a plurality of patient outcomes recorded at a plurality of successive times, and any case for which the inference engine generated a clinical decision recommendation and having at least one recorded poor patient outcome is detected as an outlier case, and
        the electronic outliers detector receives as input a prescribed patient treatment, and any case for which the prescribed patient treatment is substantially different from the clinical decision recommendation generated for the patient by the inference engine is detected as an outlier case;
    an outliers database configured to collect information pertaining to the outlier cases detecting by the electronic outliers detector; and
    an outliers report generator configured to generate a report on the outlier cases detected by the electronic outliers detector, the generated report containing at least some information collected in the outliers database;
    wherein the inference engine, the electronic outliers detector, and the outliers report generator comprise a digital device executing software.

5. The electronic CDSS as set forth in claim 4, wherein the outliers database is configured to collect physician comment regarding why a prescribed patient treatment that is substantially different from the clinical decision recommendation generated for the patient by the inference engine was prescribed.

6. The electronic CDSS as set forth in claim 1, wherein the outliers database is configured to collect names of one or more treating physicians.

7. The electronic CDSS as set forth in claim 1, wherein the outliers database is configured to collect for each patient: a clinical decision recommendation generated by the inference engine for the patient; a patient treatment prescribed for the patient; and an outcome for the patient.

8. The electronic CDSS as set forth in claim 1, wherein the revision release is further generated by (i) updating the rules developed by a plurality of medical experts based at least in part on review of the report on outlier cases, said updating not including updating the sound rule, and (ii) codifying the updated rules into software.

9. The electronic CDSS as set forth in claim 4, wherein the outliers database is configured to collect names of one or more treating physicians.

10. The electronic CDSS as set forth in claim 4, wherein the outliers database is configured to collect for each patient: a clinical decision recommendation generated by the inference engine for the patient; a patient treatment prescribed for the patient; and an outcome for the patent.

11. The electronic CDSS as set forth in claim 4, further comprising:
    a revision release configured to update at least the inference engine, the revision release comprising update software generated by (i) updating the rules developed by a plurality of medical experts based at least in part on review of the report on outlier cases, and (ii) codifying the updated rules into software.

12. A method for operating an electronic clinical decision support system(CDSS) including an inference engine comprising software configured to generate clinical decision recommendations in accordance with clinical decision rules, the method comprising:
    generating clinical decision recommendations for patient cases using the inference engine;
    detecting outlier cases comprising a subset of the patient cases for which the inference engine generated clinical decision recommendations likely to be probative of one or more potential flaws in the inference engine;
    collecting information pertaining to the outlier cases; and
    updating the inference engine to correct at least one flaw detected based on the collected information pertaining to the outlier cases, the updating including;

identifying a software error in the inference engine based on the information pertaining to the outlier cases, the software error causing the inference engine to generate clinical decision recommendations that are not in accordance with the one or more of the clinical decision rules, and removing the identified software error from the inference engine.

13. The method as set forth in claim 12, wherein the detecting comprises:

detecting an outlier case as a patient case for which the inference engine generated a clinical decision recommendation and a patient outcome was poor.

14. The method as set forth in claim 12, wherein the detecting comprises:

detecting an outlier case as a patient case for which the inference engine generated a clinical decision recommendation and a prescribed patient treatment in the patient case was substantially different from the generated clinical decision recommendation.

15. The method as set forth in claim 12, wherein the detecting comprises:

detecting an outlier case as a patient case for which at least one of the following conditions holds: (i) a patient outcome was poor, and (ii) a prescribed patient treatment was substantially different from the clinical decision recommendation.

16. The method as set forth in claim 12, further comprising:

validating the updated inference engine against the collected information pertaining to the outlier cases.

17. The method as set forth in claim 16, wherein the updating further comprises:

updating a clinical decision rule based on the information pertaining to the outlier cases; and reconfiguring the inference engine to generate clinical decision recommendations in accordance with the updated clinical decision rule.

18. The method as set forth in claim 12, further comprising:

generating a report on the outlier cases, the generated report containing at least some information collected in the outliers database, the generated report being referenced by medical experts involved in the updating.

* * * * *